United States Patent [19]

Smith et al.

[11] Patent Number: 5,088,146

[45] Date of Patent: Feb. 18, 1992

[54] CONTACT LENS CLEANING AND CONDITIONING POUCH AND METHOD OF USE

[75] Inventors: Francis X. Smith, Salem, N.H.; Stanley J. Wrobel, Andover; Manohar K. Raheja, Lowell, both of Mass.

[73] Assignee: Polymer Technology Corporation, Wilmington, Mass.

[21] Appl. No.: 545,518

[22] Filed: Jun. 28, 1990

[51] Int. Cl.⁵ .................. B08B 7/02; B08B 3/04; B08B 11/02

[52] U.S. Cl. .................... 15/104.94; 15/214; 15/244.1

[58] Field of Search ........... 15/104.94, 104.93, 214, 15/244.4, 244.3

[56] References Cited

U.S. PATENT DOCUMENTS

| 1,091,396 | 3/1914 | Serves | 15/214 |
|---|---|---|---|
| 2,176,831 | 10/1939 | Zimmerman | 15/244.4 |
| 2,761,166 | 9/1956 | Connolly | 15/104.94 |
| 3,048,878 | 9/1962 | Gray | 15/214 |
| 4,203,857 | 5/1980 | Dugan | 15/104.93 |
| 4,665,580 | 5/1987 | Morris | 15/244.4 |
| 4,779,300 | 10/1988 | Pompe | 15/104.93 |

FOREIGN PATENT DOCUMENTS 237599 2/1962 Australia .................. 15/104.93

OTHER PUBLICATIONS

Chemical Engineering 7/22/1963, p. 98.

Primary Examiner—Harvey C. Hornsby
Assistant Examiner—Terrence R. Till
Attorney, Agent, or Firm—Wolf, Greenfield & Sacks

[57] ABSTRACT

A product and method of cleaning or conditioning contact lenses is provided. Lens cleaning or conditioning is accomplished in a pouch having first and second walls between which the contact lens can be inserted along with a cleaning or conditioning solution and gently manipulated to clean or condition the contact lens surface.

9 Claims, 2 Drawing Sheets

CONTACT LENS CLEANING AND CONDITIONING POUCH AND METHOD OF USE

BACKGROUND OF THE INVENTION

Contact lenses are often treated with conditioning solutions and/or cleaning materials to condition or clean the lenses. Typical conditioning solutions include moisturizing material and eye conditioning solutions. Cleaning of contact lenses, both hard and soft, has involved difficulties.

It is important to maintain the structural integrity and optical clarity of contact lenses while applying cleaning materials in a safe and efficient manner, to thoroughly scour and clean the lenses without changing the power of the lenses or scratching the lenses in any way, and thus avoid degredation of the optical qualities of the lenses.

A variety of cleaning solutions and methods are known. Such methods include those described in U.S. Pat. No. 4,533,399 and the Background of the Invention of that patent. U.S. Pat. No. 4,533,399 describes a method of cleaning contact lenses by providing a moistened, non-woven fibrous web and rubbing the lens with the fibrous web in the presence of a cleaning solution. The patent further defines other known cleaning methods, including use of sponges of synthetic foam such as urethane, as disclosed in U.S. Pat. Nos. 3,063,083 and 4,187,574. Other sponge like products are available and are stated to be described in Japanese Kokai, JP No. 82,105,427, with still another lens cleaning method using a cleaning and polishing cloth described in U.S. Pat. No. 4,357,173.

The art has considered prior cleaning materials to have problems in some cases; as for example, lack of abrasive power to remove deposits, tendency to plug too rapidly, high cost, difficulties in handling contact lenses while still applying proper abrading power and contamination of the lens surface by allowing the skin to contact the contact lenses in certain cases.

SUMMARY OF THE INVENTION

It is an object of this invention to provide a means and method for facilitating contact lens conditioning or cleaning in a rapid and efficient manner at minimized cost and high efficiency.

Still another object of this invention is to provide a means and method in accordance with the preceeding object, where a lens can be positively positioned while a cleaning force is applied through an abrading foam material, allowing good gripping, lens feeling ability and good cleaning action without deteriorating lenses cleaned or conditioned.

It is a still further object of this invention to provide a cleaning pouch which can be used to enclose a lens, provide a conditioning and/or cleaning solution there around, with means for rubbing the inner surfaces of the pouch against the lens surfaces to provide a good cleaning and/or conditioning action, without loss of fluids used in the process prior to effective use of the fluids and wherein the cleaning or conditioning fluids act in conjunction with the pouch itself to obtain the desired result.

According to the invention, a lens cleaning or conditioning pouch for treating contact lenses is formed of a first and second sheet substantially joined together to form an enclosed inner lens chamber between the sheets, having first and second inner walls defined by the first and second sheets respectively and defining an opening of the chamber for insertion and removal of a contact lens. The first and second sheets define a peripheral edge where joined together, such that the pouch can be easily manipulated between two fingers of the user to rub the pouch inner chamber walls against a contact lens contained within the chamber. Preferably, the joint is an integral one and the sheets are integrally formed as an integral pouch. The first and second sheets are formed of an organic polymeric material having an inner open cell foam portion for applying a liquid treating material to a lens carried in the chamber and each sheet has an outer portion preventing substantial flow through of the liquid treating material to the outside. The first and second sheets each have an outside wall surface on the outside of the pouch, such that the fingers of the user move with the walls when a side to side rubbing force is exerted, causing the inside walls of the chamber of the pouch to move against and to scour the lens contained within the pouch to clean and/or condition it.

Preferably, the lens cleaning pouch has a coefficient of friction on its outside walls which is greater than the coefficient of friction of the inside walls when the inside of the sheets are wet. In addition, the sheets are preferably formed of organic foam having a skin intricately formed therewith for preventing fluid flow there through. In all cases, the lens cleaning pouch is formed of organic polymeric foam which has a barrier layer of some kind formed thereover, to prevent fluid flow to the outside of the pouch, which fluid flow could lower the coefficient of friction so that the rubbing fingers would slide on the pouch, rather than cause an abrading action of the pouch against the lens within the pouch.

According to a method of this invention, a contact lens is cleaned and/or conditioned by selecting a pouch formed of a first and second sheet joined at a peripheral edge to provide a stopping edge, a contact lens is inserted in the pouch and the first and second sheets are scoured between the fingers of the user to apply a scouring action to a lens contained within the pouch.

It is a feature of this invention that the user's fingers which would tend to slip, preventing the foam from sliding back and forth across the lens, do not slip because the outside of the pouch is maintained relatively dry, therefor acting to have the pouch inner surfaces move over the lens. The foam slides back and forth across the lens. The fact that a pouch is used, provides a surface against which the lens will be positioned during the sliding action of the fingers. Since an outer barrier or integral skin is used, the pouch prevents leakage to the outside of the conditioning solution or cleaner through the pouch. The lens can be felt through the pouch in the preferred embodiment, so that the consumer recognizes that the lens is within the pouch and can apply suitable pressure short of a damaging pressure. Because the pouch is made of an organic foam material, the pouch does not scratch or change the power of hard lens materials or even some soft lens materials used within it. Preferably, an integral outer skin is used on the polymeric material to allow some re absorption of any moisture that does find its way outside of the pouch to avoid lowering of the coefficient of friction of the outside of the pouch.

BRIEF DESCRIPTION OF THE DRAWINGS

The above and other features, objects and advantages of the present invention will be better understood from a reading of the following specification in conjunction with the attached drawings in which.

BRIEF DESCRIPTION OF PREFERRED EMBODIMENTS

Figure 1:
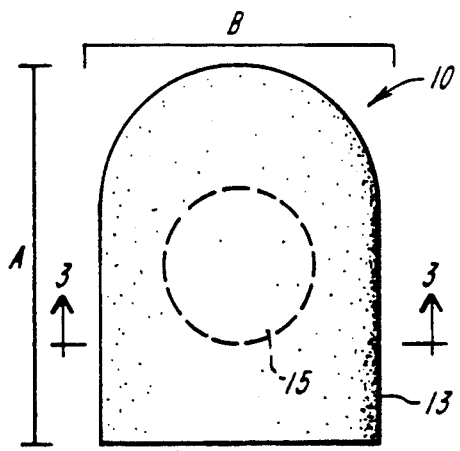
FIG. 1 is a top plan view of a pouch in accordance with a preferred embodiment of this invention.
Figure 2:
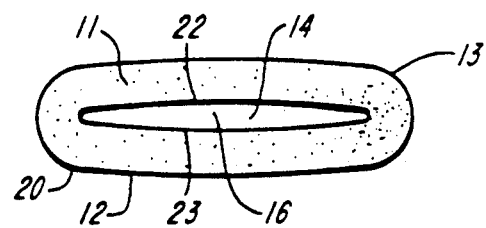
FIG. 2 is an end view thereof.
Figure 3:
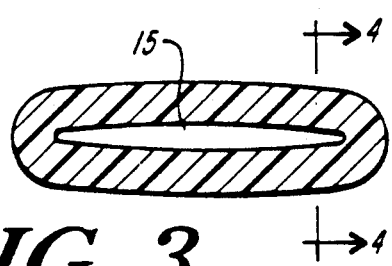
FIG. 3 is a cross sectional view through line 3—3 of FIG. 1.
Figure 5:
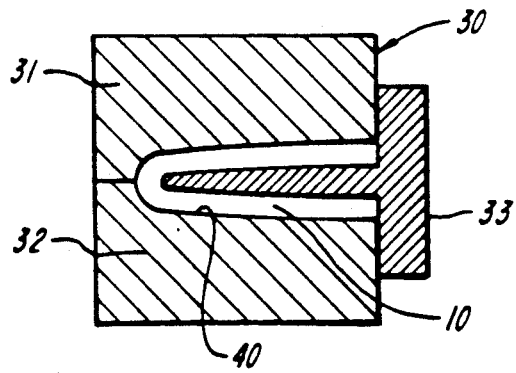
FIG. 5 is a diagramatic view through the center of a mold cavity showing a pouch being molded therein.
Figure 6:
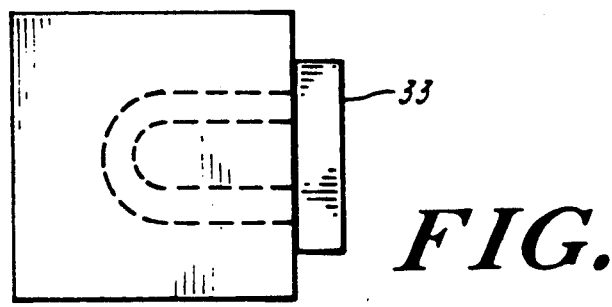
FIG. 6 is a top plan view of a mold cavity of FIG. 5.
Figure 4:
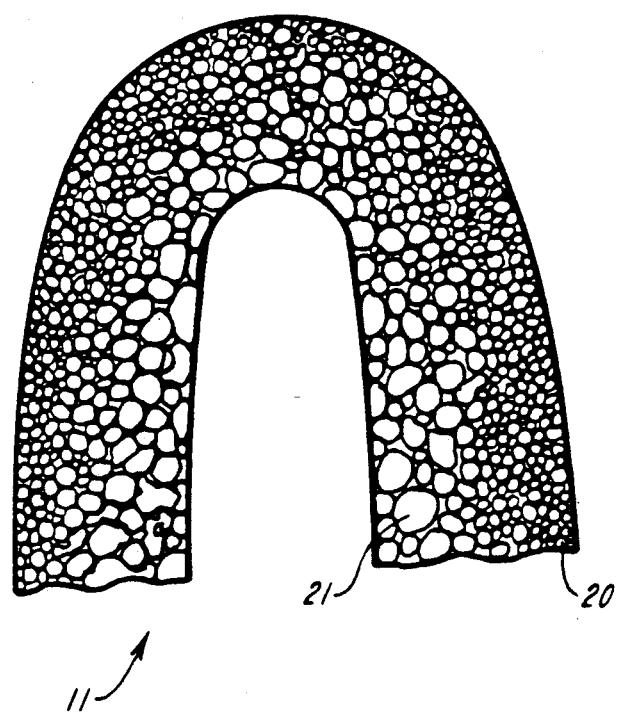
FIG. 4 is an expanded view through line 4—4 of FIG. 3, showing a cross section of the foam material forming the pouch.

A lens pouch in accordance with the present invention is shown in FIG. 1 at 10 and has a first sheet 11 and a second sheet 12 integrally joined together at a peripheral edge 13. First and second sheet, 11 and 12, form an inner enclosed lens chamber 14 which can carry a contact lens, such as a hard contact lens 15, shown in dotted outline in FIG. 1. The first and second sheets, 11 and 12, carry within chamber 14, a liquid 16 wetting the Chamber 14. The sheets 11 and 12 have an outer barrier layer 20, as best shown in the enlarged portion of sheet 11 (FIG. 4), with an inner wall portion 21. The walls 11 and 12 have inner surfaces, 22 and 23 respectively of Chamber 14, which act to rub against a contact lens 15 which may be positioned within the chamber 14 of the pouch 10.

The pouch 10 is preferably integrally formed of a molded organic polymeric material to form a foam layer wall 21, increasing in thickness with a skin layer 20 of low density foam which can act as to barrier layer to prevent flow of liquid from Chamber 14. The layer 20 extends over the entire outer surface of the pouch. The pouch preferably has a length or dimension A of from ½ to 3 inches and a width, dimension B, of from ½ to 2 inches, with a wall thickness that is thin and preferably of from 0.040 to 0.120 inch.

The particular organic polymeric foam material of the walls 11 and 12 can vary greatly. For example, while polyether polyurethanes are preferred, silicones, polyesters, polyurethanes, polystyrenes, polyolefin, polyvinylchloride, or other plastics can be used.

In all cases, the walls are resilient and compressible and have a wall thickness, density and porosity such as to be able to contain sufficient liquid to clean or otherwise condition the contact lens 15 to be conditioned or cleaned, with preferably little leakage to the outside through the walls. The liquid can be in the pouch when packaged or can be added by the user at the time of use. If packaged with the pouch, it is preferred to enclose the cleaning or conditioning fluid carrying pouch in a liquid tight envelope. The walls are non-abrasive to hard contact lenses and will not change the power of the lens under normal cleaning by finger manipulation.

In the preferred embodiment, a polyether polyurethane of the type sold by W.R. Grace Co. of New York, N.Y. under the trademark HYPOL is used. Such urethanes are described in U.S. Pat. No. 4,137,200 issued Jan. 30, 1979, which patent is incorporated by reference herein. As disclosed, hydrophyllic cross linked polyurethane foams are used which have good hydrophylic properties and can carry liquids such as surfactants and aqueous dispersions thereof. The foams are essentially made by the use of polyoxyethylene polyols used as a reactant and terminated or capped by reaction with an isocyanate. Such reactions can be carried out in inert moisture free atmospheres such as under a nitrogen blanket at atmospheric pressure at a temperature in the range of about 0° C. to about 120° C. for a period of up to about 20 hours, depending upon the temperature. The ratio of isocyanate groups to hydroxyl groups used for capping is usually between 1 to about 4 isocyanate to hydroxyl. To bring about foaming and preparation of the cross linked network final polymer of the pouch, the prepolymer or resin reactant is combined with a particular aqueous component such as water or water emulsion or water solution having water soluable materials dispersed therein. For example, suitable water soluable materials include surfactants, organic and inorganic salts, alcohols, catalyst, acids, polymer, preservatives, resins or wax dispersions, flame retardants, fungicides, fillers, blowing agents, fibers, cellulostic materials, surfactants, biostats, pigments, dyes, enzymes, proteins and the like.

In all cases, it is preferred that the materials be foamed in place to form the pouch.

In a preferred method, the materials are foamed in a mold such as 30, having an upper cavity half 31 and a lower cavity half 32, with a solid insert 33. The insert 33 is positioned and the pouch 10 can be foamed in place within the mold. Upon removal of the insert 33, the pouch can come out and be stripped from the insert 33. Alternately, the pouch may remain in cavity 40 and then be removed. When sufficient material is used within the mold cavity 40, the pouch can have an integral skin 20 formed to act as a barrier layer 20.

The barrier layer prevents water or aqueous materials, as for example surfactants, from passing from the chamber 14 through the pouch to the outside. It is desired that the coefficient of friction on the outside of the pouch, available to the hands of the user, be less than the coefficient of friction on the surface exposed to the lens 15 when both are wet. Since this enables a rubbing action to be carried out on the lens without severe finger pressures being applied to the lens which might tend to crack the lens. The barrier layer can be an increased density integral formed foam or can be a separately applied foam, cellophane, plastic, paint, coating, wax layer, lacquer, or the like. In some cases, the barrier layer is preferably of an open cell integral foam as described, which will reabsorb moisture or liquids that are exposed to the outside surface.

It is preferred that the organic foam have a density of from about 0.010 to about 0.7 gram/centimeter$^3$ to provide desired liquid holding capacity and abrasion properties when the foam is HYPOL. Tensile strengths of from 25 to 125 psi and preferrable 40 to 60 psi (ASTM D638) are preferred for the walls 11 and 12. Such foams preferably hold from 1 to 30 times their weight of water.

While the pouch is preferably an integral pouch having an edge 13 at its periphery which forms a stop for the lens during the rubbing action to prevent the lens from moving within the chamber, the pouch can be formed by sheets which are otherwise joined together about the peripheral edge 13, as by heat sealing, ultrasonic sealing, physical sewing and the like.

Hypol-type prepolymers have been found to be most desirable for forming the pouches of this invention. Hypol 2000, 2002 and 3000, as well as Hypol 5000, are useful. When aliphatic isocyanate base prepolymers are used, the pouches can be readily sterilized.

In normal formulations, one part of the polyether urethane prepolymer is mixed with 0.9 parts of an aqueous phase. The ratio can change from a 2:1 ratio of Hypol to aqueous phase through a 1:2 ratio of Hypol to aqueous phase during the foaming operation in a mold.

Various surfactants have been incorporated into the aqueous phase in order to obtain the desired characteristics of softness of cell structure in the resultant foam. Preferably, a formulation of about 0.1% to 7.5% and preferably 2% Triton X100 (Rohm and Hass Co., Philadelphia, Pa.) surfactant in the aqueous phase is used. Pouches made with higher concentrations of Triton have demonstrated a tendency for the inner surfaces to stick to each other after drying. The surfactants aid in making the resulting foam.

Useful surfactants include Pluronic (polyoxypropylene and polyoxy ethylene), a trademark product of BASF Corp. of Wyandotte, Michigan; Dapco, a trademark product of Air Products and Chemicals of Allentown, Pa.; Sipex EST30, a trademark product of Alcolac of Baltimore Md.; BRIJ 72, a trademark product of ICI Americas, Inc. of Wilmington, Del.; Lipocol SC4, a trademark product of Lipo Chem Co. of Pattersen, N.J.; and others.

Useful catalysts known in the art can supplement the molding formulation and include tertiary amine catalysts and bicarbonate catalysts.

Preferably, the molds are formed of plastics such as polypropylene or polyethylene, or have Teflon coatings over aluminum parts.

In the general process, a polyether urethane prepolymer and an aqueous solution are brought to a mixing head from two separate containers. The organic phase is maintained at a temperature of from 30° C. to 100° C., while the aqueous phase is kept at room temperature. Temperature ranges of from 10° C. to about 118° C. can be used for the organic phase, while the aqueous phase can vary from 0° C. to 90° C. Various cell structures, shape, size, open or close can be obtained by varying the temperatures of the phases, as well as the curing times.

Preferably the liquid and organic materials are mixed at about 30 to 7,000 rpm.

Male mold temperatures are preferably in the range of 93° to 100° F., with the female mold used at ambient temperature.

The temperature of the molds can vary greatly. Clamping time is preferably in the range of from 3 to 15, with 5 minutes being preferred in order to allow sufficient time for setting or final curing of the mold.

At the appropriate curing time, pouches can be removed from the mold and dried, as for example at from 40° C. to 100° C. and preferably 65° C. for from 0.5 to 6 hours. The pouches can be dried to remove excess water, but can be left with an inner aqueous solution carrying the surfactant.

The following examples are illustrative only of the invention and are not to be considered as limiting:

EXAMPLE 1

Hypol 2002 (10 g) is mixed with a 7.5% aqueous solution of Triton X-100 (9 g) using a mechanical mixer (with a three bladed steel shaft) for about 30 seconds. The mixture (about 1.7 g) was poured into the cavity of the female, high density, polypropylene mold part, which is an ambient temperature. The male part of the mold, which is made of teflon coated aluminum and is at a temperature of 95° F., is clamped to the female part. The foam is allowed to cure for 15 minutes while maintaining the temperature differential between the two mold parts. The molded pouch is removed from the mold and dried at 65° C. for 2 hours. The mold parts are thoroughly cleaned with a surfactant solution prior to next molding process.

When a mold cavity of total volume of 5.7 ml is used with a mass of reactants of 1.7 grams, the average density of the wet pouch formed is about 0.3 grams/cm$^3$.

EXAMPLE 2

The cavity of a teflon mold part is coated with multiple applications of a lacquer (eg., Red Spot Conductive IMC Lacquer, 251SL20535). About 1.7 g of a one to-one mixture of Hypol 2002 and 2% aqueous Triton X-100, which has been well mixed with a stirrer, is delivered to the coated cavity, which is at ambient temperature. The male part of the mold, which is made of teflon coated aluminum and which is at a temperature of 98° F., is clamped to the female part of the mold. The foam is cured for 10 minutes while the temperature differential between the mold parts is maintained. The demolded foam pouch is dried at 65° C. for 2 hours.

EXAMPLES 3–23

Other variations of the cleansing pouch were prepared by the processes as described in Example 1 and 2, but with variations in the formulation or processing conditions as indicated in Table 1.

TABLE 1

|  | Example 3 | Example 4 | Example 5 | Example 6 | Example 7 | Example 8 |
|---|---|---|---|---|---|---|
| Male Mold Material: | Teflon/Al | Teflon | Teflon/Al | Al | Al | Teflon/Al |
| Female Mold Material: | HDPE (high density polyethylene) | Teflon | Al | Polypropylene | Polypropylene | HDPE |
| Male Temperature: | Ambient | Ambient | Ambient | Ambient | Ambient | Ambient |
| Female Temperature: | Ambient | Ambient | Ambient | Ambient | Ambient | Ambient |
| Male Treatment: |  |  | 10% Miranol H2M 10% Sipex EST-30 |  |  |  |
| Female Treatment: |  |  |  |  |  |  |
| Prepolymer: | 10 g Hypol 2002 | 10 g Hypol 5000 | 10 g Hypol 2002 | 10 g Hypol 3000 | 10 g Hypol 2002 | 10 g Hypol 2002 |
| H$_2$O: | 10 g | 10 g | 9.5 g | 10 g | 8.59 g | 8.78 g |
| NaHCO$_3$: |  |  |  |  |  | 0.18 g |
| Triton X-100: |  | 0.5 g | 0.5 g | 1 g | 0.09 g | 0.18 g |
| Pluronic F-127: |  |  |  | 0.05 g | 0.05 g |  |
| Sipex EST-30: |  |  |  |  | 0.27 g |  |

TABLE 1-continued

Lipocol SC-4:
Dabco DC 190:
BRIJ 72:

|  | Example 9 | Example 10 | Example 11 | Example 12 | Example 13 | Example 14 |
|---|---|---|---|---|---|---|
| Male Mold Material: | Teflon/Al | Polypropylene | Noryl | Delrin | Teflon/Al | Teflon/Al |
| Female Mold Material: | Teflon | Polypropylene | Noryl | Delrin | HDPE | HDPE |
| Male Temperature: | 95° F. | Ambient | Ambient | Ambient | 93° F. | 98° F. |
| Female Temperature: | Ambient | Ambient | Ambient | Ambient | Ambient | Ambient |
| Male Treatment: |  |  |  |  |  |  |
| Female Treatment: |  |  |  |  |  |  |
| Prepolymer: | 10 g Hypol 2002 | 9 g Hypol 2002 | 9 g Hypol 2002 | 9 g Hypol 2002 | 10 g Hypol 2002 | 10 g Hypol 2002 |
| $H_2O$: | 8.78 g | 9.5 g | 9.5 g | 9.5 g | 8.6 g | 8.6 g |
| $NaHCO_3$: |  |  |  |  |  |  |
| Triton X-100: |  | 0.05 g | 0.05 g | 0.5 g |  | 0.2 g |
| Pluronic F-127: | 0.22 g |  |  |  |  |  |
| Sipex EST-30: |  |  |  |  |  |  |
| Lipocol SC-4: |  |  |  |  | 0.4 g | 0.2 g |
| Dabco DC 190: |  |  |  |  |  |  |
| BRIJ 72: |  |  |  |  |  |  |

|  | Example 15 | Example 16 | Example 17 | Example 18 | Example 19 | Example 20 |
|---|---|---|---|---|---|---|
| Male Mold Material: | Teflon/Al | Teflon/Al | Al | Al | Teflon/Al | Teflon/Al |
| Female Mold Material: | HDPE lined cavity alum. block | HDPE | HDPE | HDPE | HDPE | Polypropylene |
| Male Temperature: | 104° F. | 104° F. | 95° F. | 95° F. | 80° F. | Ambient |
| Female Temperature: | Ambient | Ambient | Ambient | Ambient | Ambient | Ambient |
| Male Treatment: |  |  | 10% Miranol H2M - 10% Sipex EST-30 | 10% Miranol H2M - 10% Sipex EST-30 | 10% Miranol H2M - 10% Sipex EST-30 |  |
| Female Treatment: |  | Polyurethane coating |  |  |  |  |
| Prepolymer: | 10 g Hypol 2002 | 10 g Hypol 2002 | 10 g Hypol 2002 | 10 g Hypol 2002 | 10 g Hypol 2002 | 20 g Hypol 2002 |
| $H_2O$: | 8.8 g | 10.2 g | 8.9 g | 7.2 g | 8.3 g | 9.25 g |
| $NaHCO_3$: |  |  |  |  |  |  |
| Triton X-100: |  | 0.8 g | 0.1 g | 1.8 g | 0.7 g | 0.75 g |
| Pluronic F-127: |  |  |  |  |  |  |
| Sipex EST-30: |  |  |  |  |  |  |
| Lipocol SC-4: |  |  |  |  |  |  |
| Dabco DC 190: | 0.2 g |  |  |  |  |  |
| BRIJ 72: |  |  |  |  |  |  |

|  | Example 21 | Example 22 | Example 23 |
|---|---|---|---|
| Male Mold Material: | Teflon/Al | Teflon/Al | Teflon/Al |
| Female Mold Material: | Polypropylene | HDPE | HDPE |
| Male Temperature: | Ambient | 95° F. | 93° F. |
| Female Temperature: | Ambient | chilled in ice | Ambient |
| Male Treatment: |  |  |  |
| Female Treatment: |  |  |  |
| Prepolymer: | 10 g Hypol 2002 | 20 g Hypol 2002 | 10 g Hypol 2002 |
| $H_2O$: | 18.5 g | 17.64 g | 8.82 g |
| $NaHCO_3$: |  |  |  |
| Triton X-100: | 1.5 g | 0.36 g |  |
| Pluronic F-127: |  |  |  |
| Sipex EST-30: |  |  |  |
| Lipocol SC-4: |  |  |  |
| Dabco DC 190: |  |  |  |
| BRIJ 72: |  |  | 0.18 g |

What is claimed is:

1. A contact lens cleaning or conditioning pouch for treating contact lenses, said pouch comprising,
a first sheet and a second sheet substantially joined together to form an enclosed inner lens chamber between said sheets having first and second inner walls defined by said first and second sheets, respectively, and defining an opening to said chamber for insertion and removal of a contact lens,
said first and second sheets defining a peripheral edge where joined together, such that the pouch can be easily manipulated between two fingers of a user to rub the pouch inner chamber walls against a contact lens contained within the chamber,
said first and second sheets being formed of an organic polymeric material having an inner open cell foam portion for applying a liquid treating material to a lens carried in said chamber and each sheet having an outer barrier portion preventing substantial flow-through of said liquid treating material to the outside,
said first first and second sheets each having an outside wall surface on the outside of said pouch, such that the fingers of a user will move with the walls when a side to side rubbing force is exerted, causing the inside walls of the chamber of said pouch to move against and to scour the lens to clean and/or condition it.

2. A contact lens cleaning pouch in accordance with claim 1, wherein the coefficient of friction of the outside walls is greater than said coefficient of friction of the inside walls when the inside of the sheets ar wet.

3. A contact lens cleaning pouch in accordance with claim 1, wherein said sheets are formed of organic foam having a skin integrally formed therewith for preventing substantial fluid flow there through.

4. A contact lens cleaning pouch in accordance with claim 1, wherein said sheets are formed of an organic foam having a barrier layer formed thereover, for preventing fluid flow therethrough to the outside of said pouch.

5. A contact lens cleaning pouch in accordance with claim 4, wherein said foam is a molded, resilient polyurethane foam having a surfactant carried therein.

6. A contact lens cleaning pouch in accordance with claim 5, wherein said polyurethane foam is an open cell foam having an outer skin which prevents substantial pass through of liquids, but which skin is open-celled and permits limited reabsorption of liquid exposed to the outside of said-pouch, said pouch chamber inner walls being non abrasive to a lens and of a hardness value such that it will not change the power of the lens under normal cleaning action by manipulation of the fingers of the user.

7. A contact lens cleaning pouch in accordance with claim 6, wherein said pouch has a length of from about one-half inches to about three inches in one direction and a width of from about one-half to two inches in another direction, with a sheet thickness of from 0.040 to 0.120 inch for each of said first and second sheets, said first and second sheets being resilient, compressable and non abrasive to a hard contact lens formed of an organic polymeric material.

8. A contact lens cleaning pouch in accordance with claim 1, wherein said sheets are formed of an organic polymeric material having an average density of from 0.010 to 0.7 gram/centimeter$^3$, and being an open cell foam material.

9. A contact lens pouch in accordance with claim 1, wherein said sheets are formed of a polyether polyurethene.

* * * * *